United States Patent [19]
Miller et al.

[11] Patent Number: 5,468,237
[45] Date of Patent: Nov. 21, 1995

[54] PRESSURE-SENSITIVE ADHESIVE AND DISPOSABLE DIAPER CLOSURE SYSTEM

[75] Inventors: John A. Miller, Woodbury; Ruben E. Velasquez Urey; Earl Tate, Jr., both of St. Paul, all of Minn.

[73] Assignee: Minnesota Mining and Manufacturing Company, St. Paul, Minn.

[21] Appl. No.: 896,415

[22] Filed: Jun. 10, 1992

Related U.S. Application Data

[63] Continuation-in-part of Ser. No. 747,745, Aug. 20, 1991, abandoned.

[51] Int. Cl.$^6$ .............................. A61F 13/15; B32B 7/12; C08L 9/00
[52] U.S. Cl. .................... 604/390; 604/389; 428/355; 525/98; 525/99; 524/505
[58] Field of Search .................... 609/385.1, 355.2, 609/389, 390; 524/505; 528/355; 525/95, 97–99

[56] References Cited

U.S. PATENT DOCUMENTS

| | | | |
|---|---|---|---|
| 2,532,011 | 11/1950 | Dahlquist et al. | 154/53.5 |
| 3,239,478 | 3/1966 | Harlan, Jr. | 260/27 |
| 3,242,110 | 3/1966 | Korpman | 260/5 |
| 3,553,051 | 1/1971 | Warrach et al. | 156/309 |
| 3,660,323 | 3/1970 | Raguse | 260/5 |
| 3,681,190 | 8/1972 | Dahlquist | 206/59 C |
| 3,932,328 | 1/1976 | Korpman | 260/27 BB |
| 3,935,338 | 1/1976 | Robertson | 427/207 |
| 3,954,692 | 5/1976 | Downey | 260/33.6 AQ |
| 4,060,503 | 11/1977 | Feeney et al. | 260/5 |
| 4,080,348 | 3/1978 | Korpman | 260/27 |
| 4,097,434 | 6/1978 | Coker, Jr. | 260/23.3 |
| 4,136,071 | 1/1979 | Korpman | 260/27 BB |
| 4,181,635 | 1/1980 | Takamatsu et al. | 260/5 |
| 4,460,364 | 7/1984 | Chen et al. | 504/387 |
| 4,540,415 | 9/1985 | Korpman | 604/390 |
| 4,719,261 | 1/1988 | Bunnelle et al. | 525/97 |
| 4,813,947 | 3/1989 | Korpman | 604/387 |
| 5,019,071 | 5/1991 | Bany et al. | 604/389 |
| 5,019,072 | 5/1991 | Polski | 604/389 |
| 5,024,672 | 6/1991 | Widlund | 604/390 |
| 5,300,057 | 4/1994 | Miller et al. | |
| 5,342,685 | 8/1994 | Gobran | |
| 5,389,438 | 2/1995 | Miller et al. | |

FOREIGN PATENT DOCUMENTS

| | | | |
|---|---|---|---|
| 0306232 | 8/1989 | European Pat. Off. | C09J 3/14 |
| 59-28236 | 7/1984 | Japan | C09J 3/12 |

*Primary Examiner*—Randall L. Green
*Assistant Examiner*—K. M. Reichle
*Attorney, Agent, or Firm*—Gary L. Griswold; Walter N. Kirn; William J. Bond

[57] ABSTRACT

A pressure-sensitive adhesive and tape are provided having a rubber component (30–60 weight percent) of polyisoprene (4–55 weight percent) blended with a styrene-isoprene-styrene block copolymer (96–45 weight percent) and a tackifying component (70–40 weight percent) to provide an adhesive that exhibits superior adhesion performance to low surface energy substrates.

25 Claims, 3 Drawing Sheets

5,468,237

PRESSURE-SENSITIVE ADHESIVE AND DISPOSABLE DIAPER CLOSURE SYSTEM

This is a continuation-in-part of application Ser. no. 07/747,745 filed Aug. 20, 1991, now abandoned.

BACKGROUND AND FIELD OF THE INVENTION

This invention relates to an improved pressure-sensitive adhesive. This adhesive is particularly useful with diaper closure tapes and the like, and more specifically, to a pressure-sensitive adhesive composition which provides improved performance characteristics when used in a diaper closure system having an adhesion surface treated with a release agent.

There are numerous patents and literature documents that are directed to the use of block copolymers and other elastomers in adhesive compositions which traditionally include the elastomer (e.g., a block copolymer such as an ABA block copolymer) and a tackifying resin. For example, U.S. Pat. No. 3,239,478 (Harlan), describes the use of an elastomeric based adhesive comprising at least 100 parts of an ABA block copolymer, a tackifying resin (25–300 parts) and an extender oil (5–200 parts). U.S. Pat. No. 3,242,110 (Korpman) describes pressure-sensitive adhesives formed from a broad group of elastomers including natural rubber and polyisoprene with a solid tackifier. The Korpman patent reports similar adhesion values for the natural rubber and the polyisoprene based adhesive.

As development of these elastomer based compositions has progressed it has been found that the adhesion properties of these adhesive compositions are extremely sensitive to the particular elastomer or elastomers used, and the proportion and type of modifiers such as solid or liquid tackifiers, aromatic or aliphatic tackifiers, plasticizers, extender oils, curing agents and the like. For example, Harlan alleged that its composition using a block copolymer and an oil achieved superior cohesive strength compared to traditional tackified natural rubber adhesives.

U.S. Pat. No. 3,681,190 (Dahlquist) describes a pressure-sensitive adhesive tape where the adhesive is substantially colorless and comprises a blend of an elastomeric polymer and an alkylated polystyrene tackifying resin. The colorless feature is attributed to the resin. Both natural rubber and polyisoprene-polystyrene based adhesive systems [Kraton™ 1107 admixed with a diblock copolymer], were exemplified. Significantly higher peel adhesions (ASTM D-1000) were reported for the block copolymer based systems.

U.S. Pat. No. 4,181,635 (Takamatsu et al.) describes a pressure-sensitive adhesive system formed from a wide range of elastomers, tackified with a low molecular weight polyisoprene (with a viscosity average molecular weight ranging from 8,000 to 77,000 with a molecular weight distribution between 1.0 and 2.7) and additional conventional tackifying resins. It is reported that polyisoprenes with high percentages of low molecular weight polyisoprene species yield adhesives that bleed and possibly lose tackiness at elevated temperatures (70° C.). Too high a molecular weight polyisoprene reportedly yields inferior low temperature (e.g., 5° C.) tack. The elastomers exemplified are masticated natural rubber and high molecular weight, cis-1,4-polyisoprene rubber.

Although there exists extensive art on the use of block copolymers in PSA compositions, due to the uncertainty in results and continuing need, the search continues for adhesive formulations with yet improved mixes of adhesion properties, such as shear strength and peel strength. Particularly, there is the continuing need for the identification of adhesive formulations that have a proper mix of adhesive properties such as would make them particularly suitable for use in closure systems such as for diapers.

SUMMARY OF THE INVENTION

It has been found that a hot melt pressure-sensitive adhesive can be provided which has advantageous adhesive and cohesive properties comprising:

(a) 30 to 60 weight percent of an elastomeric component comprised of 4–55 percent of a polyisoprene having a number average molecular weight of at least 100,000 and the remainder comprised of A-B(A) block copolymer of at least one polystyrene block A and at least one polyisoprene block B, wherein the A blocks comprise from 10% to 30% of the copolymer, and (b) a solid tackifying resin preferably admixed with, liquid tackifying resin and/or plasticizing oil so as to provide a composite midblock glass transition temperature of from about 240 to 270 Kelvin for the adhesive composition.

DETAILED DESCRIPTION OF THE PREFERRED EMBODIMENTS

Figure 1:
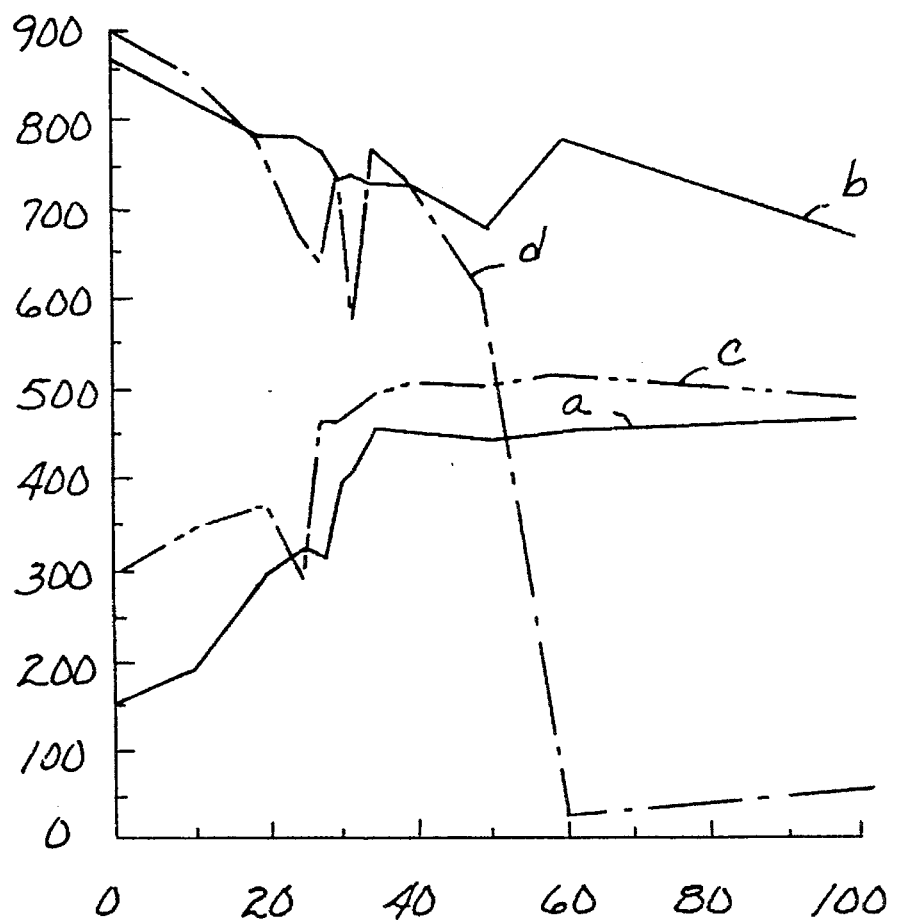
FIG. 1 is a graph of the adhesive performance versus percent isoprene for various examples.

It has been found that the addition of a relatively high molecular weight polyisoprene to a block copolymer comprising blocks of predominantly polystyrene with blocks of predominantly polyisoprene provides an adhesive having superior peel adhesion values (on an adhesive tape) to a variety of difficult to adhere to surfaces without significant loss of shear adhesion performance. The polyisoprene has a number average molecular weight of generally greater than 100,000 and preferably greater than 200,000. Generally, the polyisoprene is comprised predominantly of the cis-1,4 structure generally produced by polymerization with a Ziegler or lithium type catalyst. The polyisoprene generally comprises from 4 to 55 percent of the elastomeric component which includes the polyisoprene and the block copolymer species. Preferably, the polyisoprene is from 20 to 50 percent of the elastomeric component and most preferably 30 to 45 percent. Generally, adhesive compositions employing polyisoprene at a percentage that is greater than 55 percent had been found to retain a majority of the superior peel values, however, have shear adhesion values that are inferior for use in closure type applications where the tape is subjected to significant shear or tangential forces. Generally, however, an increase in peel performance is noted with increase in the high molecular weight polyisoprene component.

The block copolymers employed in the invention adhesive compositions fastening tabs are thermoplastic block copolymers having linear, radial or star configurations and having the A blocks and B blocks formed into what are generally termed as AB(A) block copolymers. The A block is a monoalkenyl arene, mainly polystyrene, having a molecular weight between 4,000 and 50,000, preferably between 7,000 and 30,000. The A block content is from about 10 to 50 percent, more preferably between 10 and 30 percent. Other suitable A blocks may be formed from alphamethyl styrene, t-butyl styrene and other ring alkylated styrenes as well as mixtures thereof. B is an elastomeric conjugated diene, namely isoprene, having an average molecular weight of from about 5,000 to about 500,000, preferably from about 50,000 to 200,000. Preferably, ABA triblock and AB diblock copolymers will comprise the majority of the block copolymer elastomer of the adhesive, the percent diblock being less than 95 percent of the block copolymer, preferably less than 85 percent, and most preferably less than 75 percent. At higher diblock percentages, the adhesive peel performance has been found to be smoother (non-shocky), but shear performance deteriorates, particularly at higher percent polyisoprene in the elastomeric component. Other conventional diene elastomers may be used to a minor extent, but not so as to significantly effect the adhesion properties. The block copolymer and polyisoprene as the elastomeric component is used in an amount ranging from about 30 to 60 weight percent, preferably at 35 to 55 weight percent of the functional adhesive composition.

The tackifying resin component generally comprises a blend of solid tackifying resin and liquid tackifying resin or liquid plasticizer, solid or liquid tackifying resin, or a blend of solid tackifying resin and liquid plasticizer and liquid tackifying resin. The tackifying resins can be selected from the group of resins at least partially compatible with the B blocks of the elastomeric block copolymer materials of this invention. Such tackifying resins include those aliphatic hydrocarbon resins made from the polymerization of a feed stream consisting mainly of unsaturated species containing four to six carbon atoms; rosin esters and rosin acids; mixed aliphatic/aromatic tackifying resins; polyterpene tackifiers; and hydrogenated tackifying resins. The hydrogenated resins can include resins made from the polymerization and subsequent hydrogenation of a feedstock consisting mostly of dicyclopentadiene; resins produced from the polymerization and subsequent hydrogenation of pure aromatic feedstocks such as styrene, alphamethylstyrene, vinyl toluene; resins fashioned from the polymerization and subsequent hydrogenation of an unsaturated aromatic feedstream wherein the feedstream mainly contains species having from 7 to 10 carbon atoms; hydrogenated polyterpene resins; and hydrogenated aliphatic and aliphatic/aromatic resins. Preferred tackifying resins include the aliphatic hydrocarbon resins and the hydrogenated resins. Especially preferred are the aliphatic hydrocarbon resins. The tackifying resin component can comprise the remainder of the functional adhesive composition, i.e. from 65 to 45 weight percent. If a solid tackifier is employed, generally it will comprise from 25 to 60 weight percent of the functional adhesive composition, preferably from 30 to 55 weight percent. The liquid tackifying resin correspondingly would comprise 0–30 weight percent of the functional adhesive composition, preferably from 5–20 weight percent. Using the preferred level of solid and liquid tackifiers yields adhesives with a better balance of high peel adhesion values and shear adhesion values with good initial tack.

The liquid plasticizers suitable for use in the adhesive compositions of this invention include naphthionic oils, paraffinic oils, aromatic oils, and mineral oils. Preferred plasticizing liquids include naphthionic oils and slightly aromatic oils. The oils when used are preferably used in the same relative percentages as the liquid resins in combination with the solid tackifying resin.

The adhesive preferably is tackified with solid tackifying resin with liquid plasticizer and/or liquid resin of the above described preferred types.

Preferably, the solid tackifying resin used is one that is compatible with the elastomeric conjugated diene block and is preferably a tackifying resin having a softening point between 80° and 115° C., such as is produced from polymerization of a stream of aliphatic petroleum derivatives of dienes and monoolefins having 4 to 9 carbon atoms as is disclosed in U.S. Pat. Nos. 3,932,328 and 3,954,692, the substance of which are incorporated herein by reference. Particularly preferred are tackifying resins resulting from the copolymerization of a feed comprised predominantly of $C_5$ carbon atom species such as piperylene and 2-methyl-2-butene or isoprene, commercially available, for example, as Wingtack® and Wingtack® Plus, respectively, from Goodyear Chemical Co.

The functional adhesive composition can also be modified with well known additives such as pigments, fillers, stabilizers and antioxidants for their conventional purposes.

An adhesive tape 1 is formed by placing the adhesive 3 described above on a conventional substrate 2. The substrate can suitably be formed of a synthetic polymer such as polyolefins (e.g., polypropylene), polyesters, polyamides or the like. Natural backings such as Kraft paper backings may also be used. The adhesive can be applied by any conventional method including melt coating, gravure, coextrusion, solvent coating and the like.

The CMTg of the adhesive composition can be calculated using the Fox Equation from measuring the Tg of the midblock of the elastomeric block copolymer and the measured Tg of each tackifying resin, polyisoprene and liquid plasticizer oil. The Tg for each component is measured using a differential scanning calorimeter such as a DSC-7, manufactured by Perkin-Elmer. The Tg is measured on the second heating run using a scan rate of 20 degrees Centigrade per minute. The first heating run is made up to well above the softening point of the test material. The sample is subsequently quenched to well below the Tg of the material. Antioxidants added to the adhesive are not figured into the calculation of the CMTg. The Fox Equation is:

$$\frac{\Sigma_i W_i}{CMTg} = \Sigma_i \frac{W_i}{Tg_i}$$

where $W_i$ is the weight fraction of component i and $Tg_i$ is the glass transition temperature of component i. Only the midblock portion of the block copolymer is included in the calculation of the CMTg. For a styrene/isoprene block copolymer, the midblock is the polyisoprene portion of the molecule.

The CMTg can be used to design adhesive compositions having the described high peel values, with accompanying shear performance and high initial tack. Generally the CMTg of the adhesive should range from 240 to 270K and preferably from 245 to 255K. The most preferred CMTg values provided preferred levels of peel adhesion. The preferred 135° peel values are at least about 300 grams/in. and higher, and preferably at least 400 grams/in., to difficult to adhere to surfaces such as embossed polyethylene or low adhesion backsize (LAB) coated films or substrates. The high peel adhesion is also accompanied by excellent smooth peel performance compared to adhesive compositions without the polyisoprene. Generally the composition when coated at typical coating weights of 12 grains/24in.² (50 micrometers) or less will have a ratio of average peak height to average peel level, for a peel trace, of less than 1.7 and preferably less than 1.3 to a smooth substrate, such as LAB coated polypropylene.

The $CMT_g$ values described above, although an excellent predictor of peel behavior for a given percent polymer adhesive composition, may not adequately predict peel and shear performance with respect to certain non-preferred tackifiers and tackifying systems. For these systems, shear can be raised within the teachings of this invention by increasing the elastomer and/or solid resin content of the adhesive composition used within the outlined $CMT_g$ ranges.

Figure 4:
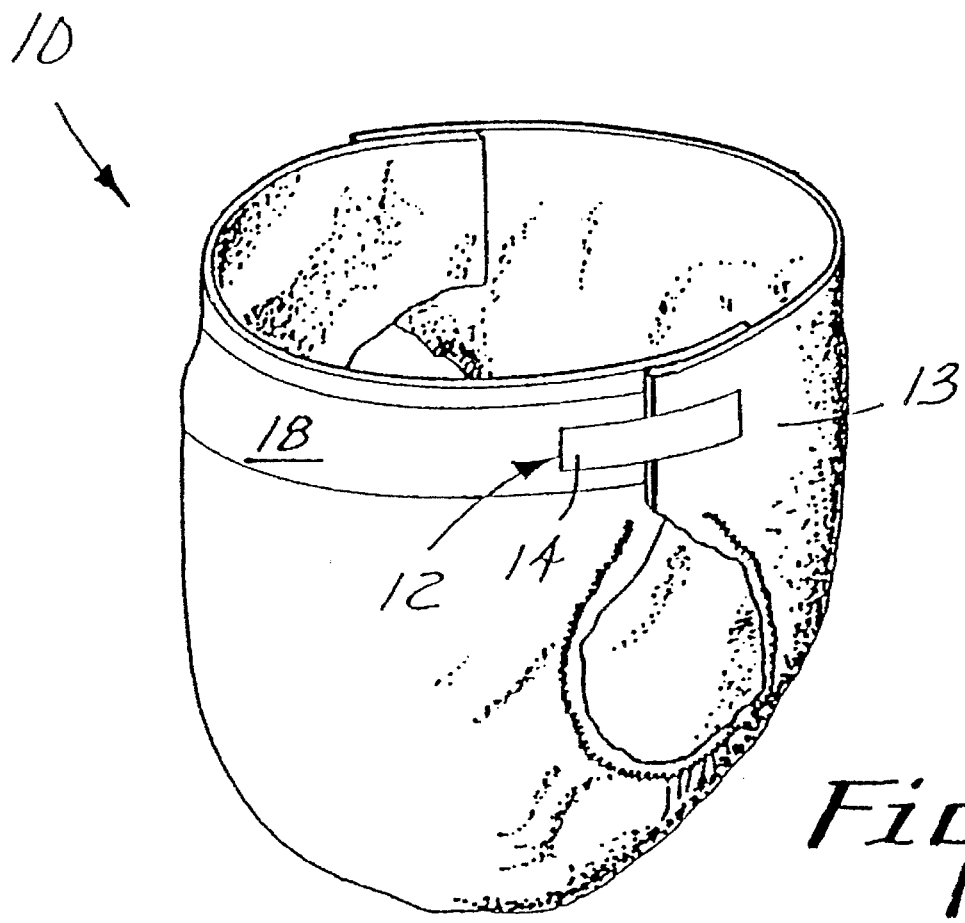
FIG. 4 is a standard diaper and fastening tape using the invention adhesive.
Figure 3:
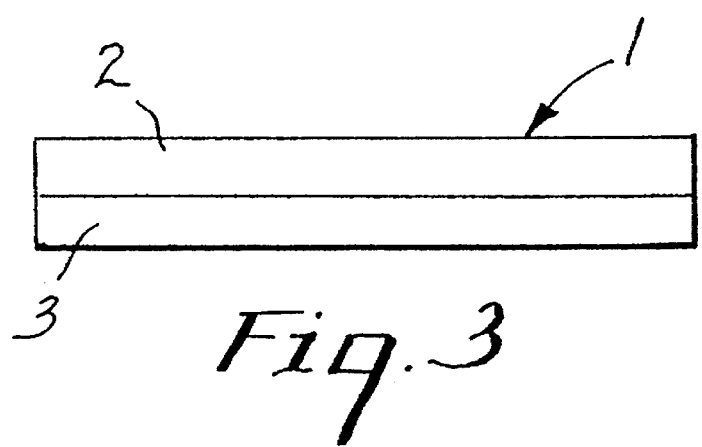
FIG. 3 is a tape.

The invention adhesive can advantageously be used (FIG. 4) on an adhesive fastening tab 12 to effect closure of the baby diaper or adult incontinence device 10, by attachment to a Low Adhesion Backsize (LAB) treated polyolefin or like reinforcement film or surface 18. The reinforcing film 18 is typically attached to a liquid impermeable outer shell 13 of the diaper in a reinforced area where the fastening tab adheres to the diaper. These reinforcing films are generally formed of a relatively stiff polymer film, such as a polypropylene film. These reinforcing films are also typically supplied as a tape in a roll form with the adhesive preapplied. In order to unroll the tape from the roll the tapes are provided with what is termed a Low Adhesion Backsize (LAB) by chemical or like treatment.

A typical LAB treatment is a urethane coating. However, reinforcing film cut from these LAB-treated tapes complicates adhesive diaper closure systems by interfering with subsequent adhesion of the fastening tab, making the selection of the appropriate adhesive to use on the fastening tab difficult.

Two important aspects of fastening tab performance in a diaper, or the like, adhesive closure system are shear resistance and peel strength performance. Peel strength is important in terms of adhesive fastening tape performance and customer perception of performance. A low peel strength bond increases the risk of popping open when subjected to the forces encountered during use. Further, low peel strengths are often associated with shocky peels (generally tested at a peel rate of 12 inches per minute). Shocky peels are well understood in the art and are when the tape peels in a jerky and noisy (sounding somewhat like a zipper) manner. The adhesive fastening tab of this invention exhibits consistently high peel values to LAB treated substrates, e.g., at least about 300 grams per inch to a common urethane LAB treated smooth polyolefin film. These consistent, substantially non-shocky peels are extremely advantageous in an adhesive closure system.

The high peels obtainable with the invention adhesive tapes occasionally exceed 750 grams per inch, however, not excessively such as to be perceived as a problem. Further this can be countered by use of more adhesive release agents as the low adhesion backsize making the tape easier to handle in the manufacturing process.

The shear force resistance for a commercial adhesive fastening tab is preferably at least 200 minutes and more preferably at least 300 minutes with a 1 kilogram weight. Shear resistances of less than 300 down to about 100 are still nominally functional yet are not commercially desirable.

The preferred adhesive coating thickness ranges from 20 to 75 microns, preferably from 25 to 50 microns. With too thin of an adhesive layer thickness, the adhesion properties will be adversely affected, whereas excess coating thicknesses can be wasteful.

A further aspect of the invention adhesive formulation is that, it is generally suited to hot-melt coating techniques, which is advantageous in terms of environmental impact.

The following examples are the currently contemplated preferred modes for carrying out the invention and should not be considered as limiting thereof unless otherwise indicated. Examples 1 to 13

The samples were prepared by coating the adhesives as listed in Table 1 onto cast polypropylene films, exhibiting a matte finish. For the examples, the polypropylene film was 4 mils (100 microns) thick and the adhesives were applied from a 25% to 50% solids solution in toluene and heptane in a conventional fashion. For each adhesive, 1% by weight of Irganox™ 1010, a hindered phenol antioxidant available from Ciba-Geigy, was added.

The resulting adhesives had the following compositions (the values in parentheses in Table 1 represent the weight percent of that particular component in the adhesive composition):

TABLE I

| Exp. | $CMT_g$ | Liquid[1] | Solid Resin[2] | Elastomer Total | Percent Polyisoprene |
|---|---|---|---|---|---|
| C1 | 250.5 | 13.55 | 41.45 | 45.00 | 0 |
| 2 | 250.5 | 13.15 | 41.85 | 45.00 | 10 |
| 3 | 250.5 | 12.70 | 42.30 | 45.00 | 20 |
| 4 | 250.5 | 12.50 | 42.50 | 45.00 | 25 |
| 5 | 250.5 | 12.40 | 42.60 | 45.00 | 27.5 |
| 6 | 250.5 | 12.30 | 42.70 | 45.00 | 30 |
| 7 | 250.5 | 12.30 | 42.70 | 45.00 | 32 |
| 8 | 250.5 | 12.15 | 42.85 | 45.00 | 35 |
| 9 | 250.5 | 11.90 | 43.10 | 45.00 | 40 |
| 10 | 250.5 | 11.50 | 43.50 | 45.00 | 50 |
| C11 | 250.5 | 11.10 | 43.90 | 45.00 | 60 |
| C12 | 250.5 | 9.50 | 45.50 | 45.00 | 100 |
| 13 | 250.5 | 12.30 | 42.70 | 45.00 | 32 |

[1]Shellflex ™ 371
[2]Wingtack ™ Plus

The elastomer was a blend of Kraton™1111 (a polyisoprene-polystyrene block copolymer blend) and polyisoprene (Cariflex™ IR-309, available from Shell Chemical Co., which has a number average molecular weight of 390,000). The total elastomer column refers to the amount of polyisoprene and block copolymer used in the adhesive, whereas the polyisoprene column indicates the percentage of the total elastomer that is polyisoprene.

The examples were then tested for their shear and 135° peel, using no rolldown pressure (NRP) and a rolldown (RD) pressure of 4.5 lbs. on to a smooth frontal tape surface of biaxially oriented polypropylene (BOPP) having low adhesion backsize (LAB) coating, and a matte finish cast polyethylene film typical of that found on disposable diapers. The LAB was a copolymer of vinyl acetate and vinyl alcohol where some of the alcohol groups in the polymer backbone have been reacted with octadecyl isocyanate, as described in U.S. Pat. No. 2,532,011. The adhesive thickness for all examples was around 11 grains/24 in.² (46 micrometers). The results are depicted in Table II for the BOPP and in TABLE III for the cast polyethylene.

TABLE II

| Example | 135° Peel (RD) | 135° Peel (NRD) | Shear | Shocky |
|---|---|---|---|---|
| C1 | 298 | 151 | 898 | S |
| 2 | 347 | 179 | 855 | S |
| 3 | 371 | 292 | 774 | S |
| 4 | 289 | 316 | 667 | S |

TABLE II-continued

| Example | 135° Peel (RD) | 135° Peel (NRD) | Shear | Shocky |
| --- | --- | --- | --- | --- |
| 5 | 470 | 304 | 634 | SP |
| 6 | 470 | 389 | 736 | SP |
| 7 | 480 | 405 | 574 | SP |
| 8 | 499 | 450 | 774 | SS |
| 9 | 508 | 446 | 736 | SM |
| 10 | 505 | 435 | 603 | SM |
| C11 | 519 | 445 | 24 | SM |
| C12 | 491 | 460 | 51 | SM |
| 13 | | 414 | | |

TABLE III

| Example | 135° Peel (RD) | 135° Peel (NRD) |
| --- | --- | --- |
| C1 | 877 | 855 |
| 2 | 882 | 816 |
| 3 | 919 | 773 |
| 4 | 903 | 775 |
| 5 | 884 | 764 |
| 6 | 859 | 726 |
| 7 | 809 | 736 |
| 8 | 857 | 724 |
| 9 | 859 | 719 |
| 10 | 847 | 672 |
| C11 | 854 | 773 |
| C12 | 938 | 658 |
| 13 | 861 | 771 |

The shear values are reported in minutes and the 135° peels are reported grams per inch. FIG. 1 plots the shear and peel values where a represents the 135° peel from BOPP with no rolldown (NRD), b represents the 135° peel from polyethylene with NRD, c represents the 135° peel from BOPP with a rolldown and d represents the shear values from BOPP. The horizontal axis represents the percent polyisoprene and the vertical axis represent the peel or shear values. As can be seen, the peel values from BOPP rise rapidly then remain at a relatively high level at approximately 30 percent polyisoprene. The shear values in contrast dropped significantly for compositions with over about 50 percent polyisoprene.

A further advantageous effect is seen in that the peels to polyethylene do not proportionally rise with the peels to BOPP, rather they drop slightly. A feature advantageous for diaper applications where a reinforcing strip of BOPP is placed on a thin polyethylene film. For diapers of this construction it is preferred that the relative peel of BOPP be high compared to the peel to the thin polyethylene film so as not to tear the backsheet when the target strip of BOPP is missed.

Shockyness was tested subjectively with S representing shocky, SP representing some peaks, SS is slightly shocky and SM is smooth where the progression in shockyness is S to SP to SS to SM.

(S) A shocky peel is defined as having peaks and valleys (load drop) with significant and consistent frequency.

(SM) A smooth peel is defined as a peel without significant load drops.

(SP) A smooth peel containing 2–3 shocky peaks throughout the trace.

(SS) A slightly shocky peel has a mixture of smooth and shocky peel portions throughout the trace.

Figure 2:
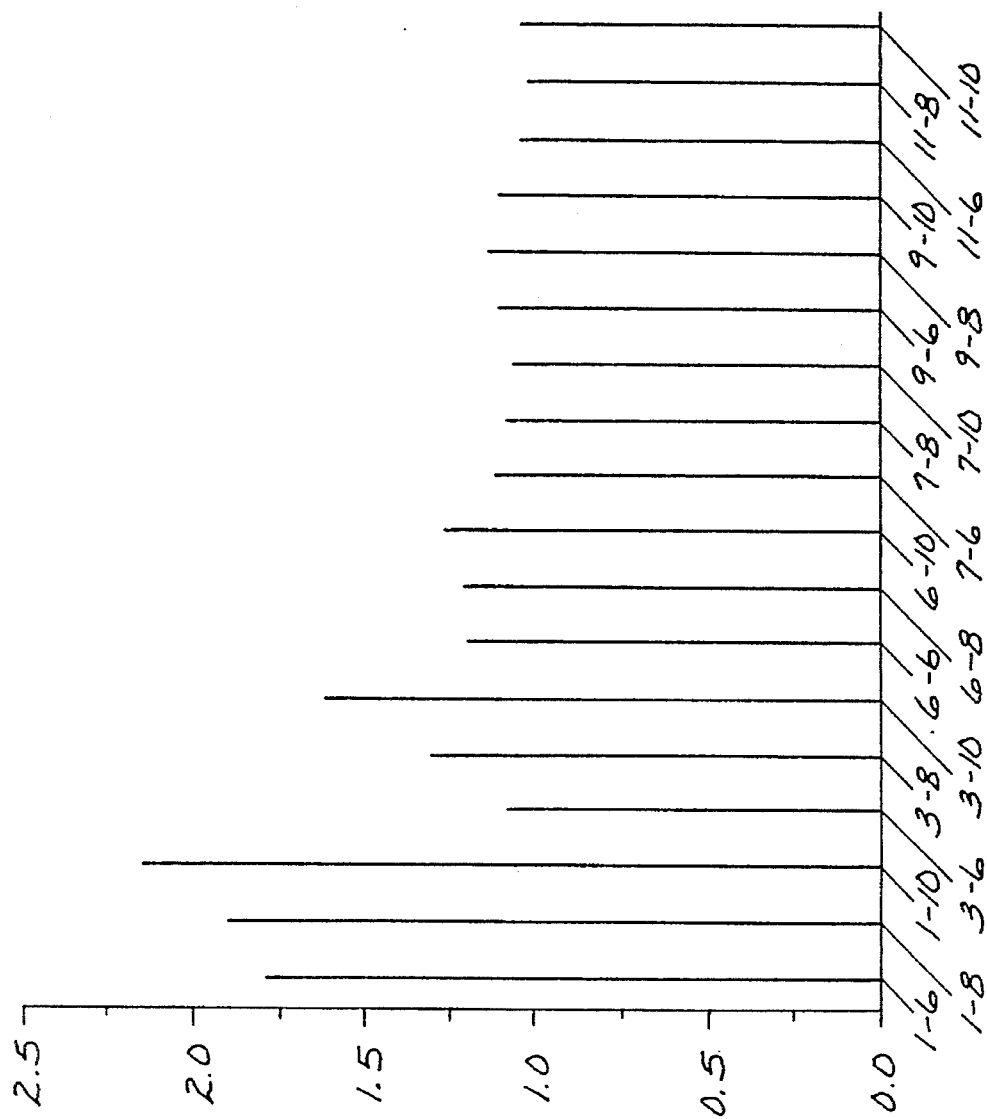
FIG. 2 is a plot of the ratio of average peaks-to-average peels for peel traces.

The shockyness of the examples was also tested at various adhesive coating weights using a digital tensile instrument (Instron: Model 4501) and a data acquisition and analysis software package (Series IX) from Instron. 135° peel data from BOPP were analyzed to find the average of the peaks (peak is defined as having a load drop >1%) and the average of the trace (average trace is defined as the area under the curve). The shockyness is quantified by the ratio of the average peak-to-the average trace. The results of this test are shown in FIG. 2. The vertical axis represents the ratio of average peak height-to-average peel level of the trace. A perfectly smooth peel would have a ratio of 1. The horizontal axis represents the example number and coating weight. For instance, "1–6" represents Example 1 at an adhesive coating thickness of 6 grains/24 in.$^2$ (25 micrometers). The adhesive was applied using no rolldown. The drop in shockyness is apparent at polyisoprene and becomes more pronounced at low coating weights.

EXAMPLES 14–21

These examples were prepared as per Examples 1–13 above and applied at a coating weight of 12 grains/24 in.$^2$ (50 micrometers). The samples were tested using the 135° peel test at different peel rates using a BOPP test substrate with an LAB coating at rolldowns of 4.5 lbs. (2040 grams) and 100 grams. The peel rate was varied from inches/minute (30.5 cm/minute) to 100 inches/minute (254 cm/minute). The tape adhesive compositions are given in Table IV below. All percentages are in absolute weight percent.

TABLE IV

| Example | $CMT_g$ | Poly-isoprene[1] | Block Copolymer[2] | Oil[3] | Solid Resin[4] |
| --- | --- | --- | --- | --- | --- |
| C14 | 250.5 | 0 | 42.0 | 16 | 42.0 |
| 15 | 250.5 | 4.2 | 37.8 | 15.7 | 42.3 |
| 16 | 250.5 | 12.6 | 29.4 | 14.9 | 43.1 |
| 17 | 250.5 | 21.0 | 21.0 | 14.1 | 43.9 |
| C18 | 254.9 | 0 | 40.0 | 13.8 | 46.2 |
| 19 | 254.9 | 4.0 | 36.0 | 13.4 | 46.6 |
| 20 | 254.9 | 12.0 | 28.0 | 12.6 | 47.4 |
| 21 | 254.9 | 20.0 | 20.0 | 11.8 | 48.2 |

[1]Cariflex ™ IR-309
[2]Kraton ™ 1111
[3]Shellflex ™ 371
[4]Wingtack ™ Plus

The 135° peel results (in grams/in.) at various peel rates with a 4.5 lb. rolldown are shown in Table V.

TABLE V

| Example | 12 in/min | 50 in/min | 100 in/min |
| --- | --- | --- | --- |
| C14 | 327 | 106 | 83 |
| 15 | 393 | 118 | 115 |
| 16 | 428 | 211 | 138 |
| 17 | 415 | 307 | 173 |
| C18 | 152 | 75 | 83 |
| 19 | 203 | 66 | 54 |
| 20 | 328 | 118 | 65 |
| 21 | 466 | 147 | 113 |

The 135° peel values against LAB coated BOPP at various peel rates with a 100 gram rolldown is set forth in Table VI.

TABLE VI

| Example | 12 in/min | 25 in/min | 50 in/min |
| --- | --- | --- | --- |
| C14 | 299 | 227 | 126 |
| 15 | 328 | 262 | 144 |
| 16 | 376 | 386 | 248 |
| 17 | 368 | 424 | 399 |

TABLE VI-continued

| Example | 12 in/min | 25 in/min | 50 in/min |
|---|---|---|---|
| C18 | 184 | 92 | 62 |
| 19 | 171 | 136 | 79 |
| 20 | 331 | 178 | 112 |
| 21 | 450 | 361 | 164 |

Tables V and VI show that the addition of polyisoprene to the rubber block copolymer component of the adhesive provides enhanced peel adhesion values, even at rapid peel rates.

EXAMPLE 22 to 29

Tape samples were prepared as described above for Examples 1 to 13 with a total adhesive thickness of 7 grains/24 in.$^2$ (29 micrometers). The adhesive compositions are given in weight percent in Table VII below.

TABLE VII

| Example | Block Copolymer[1] | Poly-isoprene[2] | Liquid Oil[3] | Solid Resin[4] | $CMT_g$ |
|---|---|---|---|---|---|
| 22 | 30 | 20 | 14.8 | 35.2 | 243 |
| 23 | 30 | 20 | 12.8 | 37.1 | 245 |
| 24 | 30 | 20 | 10.9 | 39.1 | 247 |
| 25 | 30 | 20 | 9.0 | 41 | 249 |
| 26 | 30 | 20 | 6.2 | 43.8 | 252 |
| 27 | 30 | 20 | 3.5 | 46.5 | 255 |
| 28 | 30 | 20 | 0.9 | 49.1 | 258 |
| 29 | 23.7 | 20 | 0 | 56.3 | 265 |

[1]Kraton ™ 1111
[2]Cariflex ™ IR-309
[3]Shellflex ™ 371
[4]Wingtack ™ Plus

These tapes were evaluated with regard to their 135° peels as per Examples 1–13, against a biaxially oriented polypropylene film with an LAB, and a matte finish cast polypropylene film with an LAB. Shear results in minutes are also given for the polypropylene surfaces. The results are shown in Table VIII.

TABLE VIII

| Example | BOPP | Shear BOPP | Cast PP | Shear Cast PP |
|---|---|---|---|---|
| 22 | 357 | 150 | 231 | 20 |
| 23 | 388 | 290 | 261 | 50 |
| 24 | 424 | 450 | 287 | 100 |
| 25 | 440 | 700 | 320 | 120 |
| 26 | 404 | 1,400 | 386 | 300 |
| 27 | 415 | 1,400 | 364 | 450 |
| 28 | 320 | 1,400 | 391 | 1,100 |
| 29 | 242 | 1,400 | 350 | 520 |

This series of examples demonstrates the effect of the variation of adhesive $CMT_g$ on the adhesive properties of the tapes.

EXAMPLES 30 to 35

These examples were prepared in accordance with the procedure of Examples 1 to 13, with the exception of Example 35, which was hot melt coated. The adhesive coating weights and the adhesive compositions are indicated in Table IX below, and show the effect of using different types and molecular weight polyisoprenes.

TABLE IX

| Example | C.W. | $CMT_g$ | % Block Copolymer[1] | % Polyisoprene | % Liquid Oil[7] | % Solid Resin[8] |
|---|---|---|---|---|---|---|
| 30 | 10 | 240.3 | 29.6 | 27.4[2] | 11 | 32 |
| 31 | 12 | 254.0 | 21.5 | 21.5[3] | 10 | 47 |
| 32 | 12 | 254 | 26 | 26[3] | 2.2 | 45.8 |
| 33 | 11 | 247 | 25 | 25[4] | 13 | 37 |
| 34 | 11 | 250.5 | 30.6 | 14.4[5] | 12.3 | 42.7 |
| 35 | 12 | 250.5 | 30.6 | 14.4[6] | 12.3 | 42.7 |

[1]Kraton ™ 1111
[2]Cariflex IR-305, $\overline{Mn}$ = 750,000
[3]Polyisoprene, number average molecular weight ($\overline{Mn}$) is 150,000, $T_g$ = 215K
[4]Polyisoprene, $\overline{Mn}$ is 200,000, $T_g$ = 215K
[5]Cariflex ™ IR-309
[6]Cariflex ™ IR-500
[7]Shellflex ™ 371
[8]Wingtack ™ Plus The 135° peel and shear data for these examples was obtained against BOPP and matte finish cast polypropylene films, each with an LAB. The results of which are shown in Table X.

TABLE X

| Example | Peel BOPP | Shear BOPP | Peel Cast | Shear Cast |
|---|---|---|---|---|
| 30 | 320 | 1,080 | — | — |
| 31 | 600 | 20 | 700 | 20 |
| 32 | 220 | 990 | 750 | 500 |
| 33 | 690 | 710 | — | — |
| 34 | 650 | 1,270 | 520 | 220 |
| 35 | 620 | 389 | 592 | 126 |

The peel performance is generally good with the high $\overline{Mn}$ polyisoprene compositions providing improved shear performance.

EXAMPLES 36 to 39

These samples were prepared in accordance with the procedure of Examples 1 to 13. The tapes were coated to 12 grains/24 in.$^2$ with the exception of Example 36 which had adhesive coated at 9 grains/24 in.$^2$ (38 microns). The adhesive compositions are set forth in Table XI below.

TABLE XI

| Example | $CMT_g$ | % Block Copolymer[1] | % Poly-isoprene[2] | Liquid Resin | Solid Resin |
|---|---|---|---|---|---|
| 36 | 251 | 37.8 | 16.2 | 6.6[3] | 39.4[6] |
| 37 | 251 | 37.8 | 16.2 | 10.1[4] | 35.9[7] |
| 38 | 251 | 37.8 | 16.2 | 7.9[4] | 38.1[8] |
| 39 | 251 | 37.8 | 16.2 | 7.6[5] | 38.4[8] |

[1]Kraton ™ 1111
[2]Cariflex ™ IR-309
[3]ECR ™ 143H
[4]Escorez ™ 2520
[5]Zonarez ™ A-25
[6]Arkon ™ P-90
[7]Regalite ™ 355
[8]Escorez ™ 1310

The 135° peel and shear data was obtained against BOPP and cast polypropylene films, each with an LAB. The results of which are set forth in Table XII.

TABLE XII

| Example | 135° Peel BOPP | Shear BOPP | 135° Peel Cast PP | Shear Cast PP |
|---|---|---|---|---|
| 36 | 320 | 1,400 | 290 | 100 |
| 37 | 410 | 1,400 | 450 | 320 |
| 38 | 380 | 1,400 | 670 | 430 |
| 39 | 340 | 1,400 | 610 | 770 |

COUNTEREXAMPLE 40

A standard natural rubber base adhesive tape, 3M product Y-9377, used as a release tape for disposable diapers, was tested for 135° peel and shear performance against BOPP and matte finish cast polypropylene films with an LAB. The natural rubber was tackified with solid resin. The 135° peels were tested with a rolldown (RD) of 4.5 lbs. and without any rolldown (NRD). The peel from BOPP was 47 grams/in with no rolldown and 113 grams/in with rolldown. The peel from the cast matte polypropylene film was 174 grams/in. with no rolldown and 430 grams/in. with a rolldown. All the peels were shocky.

EXAMPLES 41–52

These examples were prepared in accordance with the procedure of Examples 1–13 with a total adhesive thickness of 10 grains/24 in$^2$ (42 micrometers). The adhesives all had a CMTg of 250.5 Kelvin. The block copolymer used was an admixture of Kraton™ 1111 and pure diblock copolymer of uncoupled Kraton™ 1111 to provide a block copolymer with the indicated total percent diblock (the remaining fraction being essentially triblock copolymer). The adhesive polymer portion compositions are given in weight percent in Table XIII below. Liquid plasticizer comprised 11.5 weight percent of Examples 47–52 and 12.3 weight percent of Examples 41–46. The liquid was Shellflex™ 371 oil. The solid resin was Wingtack™ Plus and comprises 43.5 weight percent of Examples 47–52 and 42.7 weight percent of Examples 41–46.

TABLE XIII

| Example | Total Polymer Percent Weight | Percent Polyisoprene[1] | Percent[2] Block Copolymer | Percent Diblock |
|---|---|---|---|---|
| 41 | 45 | 50 | 50 | 20 |
| 42 | 45 | 50 | 50 | 40 |
| 43 | 45 | 50 | 50 | 60 |
| 44 | 45 | 50 | 50 | 75 |
| 45 | 45 | 50 | 50 | 85 |
| C46 | 45 | 50 | 50 | 100 |
| 47 | 45 | 30 | 70 | 20 |
| 48 | 45 | 30 | 70 | 40 |
| 49 | 45 | 30 | 70 | 60 |
| 50 | 45 | 30 | 70 | 75 |
| 51 | 45 | 30 | 70 | 85 |
| 52 | 45 | 30 | 70 | 100 |

[1]Cariflex ™ IR-309, percent of the total polymer
[2]Percent of the total polymer The adhesive compositions in Table XIII were then tested for 135° peel and shear performance against BOPP as set forth in Table XIV below.

TABLE XIV

| Example | 135° Peel | Shear |
|---|---|---|
| 41 | 433 | 312 |
| 42 | 412 | 301 |
| 43 | 443 | 192 |
| 44 | 447 | 146 |
| 45 | 446 | 103 |
| C46 | 463 | 58 |
| 47 | 392 | 932 |
| 48 | 424 | 1109 |
| 49 | 451 | 1320 |
| 50 | 438 | 944 |
| 51 | 432 | 1288 |
| 52 | 466 | 126 |

The results show that the peel performance was uniformly high for all of Examples 41–52. Shear performance was also generally superior when the percent isoprene was in the middle of the preferred range at 30% of the total polymer. At the edge of the preferred percent polyisoprene range, the shear performance dropped significantly, but generally was still functional. However, the shear performance was unacceptable when the block copolymer portion was pure diblock at higher percent isoprene, Counterexample 46. At lower percent polyisoprene, the shear performance was still nominally functional, even with the pure diblock, Example 52, however, shear performance was markedly inferior to the adhesive examples having at least a portion of triblock copolymer in the block copolymer portion of the total polymer (elastomer), Examples 47–51.

135 Degree Peel from Frontal Tape

The peel adhesion test is a 135° peel from a smooth frontal tape surface of biaxially oriented polypropylene (BOPP) or a matte cast polypropylene, having an LAB on it, or from a matte polyethylene surface used for a disposable diaper backsheet with no LAB. The peel rate is 12 inches per minute unless otherwise indicated. The tape samples are rolled down onto the test substrate using two passes of a 4.5 pound roller a 100 gm roller or no roller. This test is a variation on PSTC-5. The data is reported in grams per inch and was run at 70° F. and 50 percent relative humidity.

Shear from Frontal Tape Substrate

The shear adhesion is measured by determining the length of time it takes for a 1 inch by 1 inch sample to shear off a frontal tape test substrate under a 1 kilogram load. The frontal tape is either a smooth frontal tape(BOPP) with a LAB as described above or a cast matte polypropylene(PP) with a LAB. Alternatively, a matte polyethylene diaper film can be used. The 2" by 6" piece of frontal tape is laminated to a 2" by 6" piece of reinforcing tape (3M Y-9377) in order to enhance the stiffness of the substrate. On the side opposite the reinforcing tape, a one by two inch area of the test tape is rolled down onto the test substrate using 2 passes of a 4.5 pound roller. The overlap area between the test tape and the test substrate is one by one inch. The laminated substrate and the test tape are hung vertically in a 40° C. oven for 15 minutes after which a 1 kilogram weight is hung from the test tape, generating a shear load at a 180° angle. The time in minutes for the weight to drop is used as the measure of the shear adhesion.

Shellflex™ 371 is a naphthenic oil having about 10% aromatics measured by clay-gel analysis having a Tg of 209 Kelvin and is available from Shell Chemical Co.

Wingtack™ Plus is a solid $C_5$ tackifying resin with a Tg of 315 Kelvin available from Goodyear Chemical Co.

Kraton™ 1111 is a polystyrene-isoprene linear block copolymer available from Shell Chemical Company having a styrene content of about 22 percent, and a midblock Tg of about 215 Kelvin.

Escorez™ 1310 is a solid C₅ tackifying resin available from Exxon Chemical Corp. having a Tg of 313.5 Kelvin.

Zonarez™ A-25 is a liquid alpha pinene tackifying resin with a Tg of 251 Kelvin available from Arizona Chemical Co.

ECR™ 143H is a hydrogenated aliphatic hydrocarbon resin with a Tg of 247 Kelvin available from Exxon Chemical Corp.

Escorez™ 2520 is a hydrogenated aliphatic hydrocarbon resin with a Tg of 2513 Kelvin available from Exxon Chemical Corp.

Regalite™ 355 is a hydrogenated rosin acid with a Tg of 318.1 Kelvin available from Hercules Inc.

Cariflex™, IR-309 is a polyisoprene rubber having a number average molecular weight of 390,000 and a $T_g$ of 215K available from Shell Chemical Co.

Cariflex™, IR-500 is a polyisoprene rubber having a number average molecular weight of 390,000 and a $T_g$ of 215K available from Shell Chemical Co.

Arkon™P-90, a hydrogenated resin with a $T_g$ of 309K available from Arakawa Chemical Co.

Other embodiments of the invention will be apparent to those skilled in the art from the consideration of the specification of or practice of the invention disclosed herein. It is intended that the specifications and examples be considered as exemplary, with the true scope and spirit of the invention being indicated by the following claims.

We claim:

1. A pressure-sensitive adhesive composition comprising a functional adhesive mixture of;
   30 to 60 weight percent of an elastomeric component consisting essentially of 4 to 55 percent polyisoprene having a number average molecular weight of greater than 100,000 and 45 to 96 percent of an AB(A) block copolymer wherein the A block is 10 to 50 percent of the copolymer and comprises a ring alkylated styrene or styrene and the B block is derived primarily from isoprene, said block copolymer comprising less than 95 weight percent diblock copolymer, and
   70 to 40 weight percent of a tackifying component comprising solid tackifying resin, solid tackifying resin with a liquid tackifying resin or plasticizing oil, or a solid tackifying resin with liquid tackifying resin and plasticizing oil so as to provide an adhesive mixture having a composite midblock glass transition temperature in the range of 240 to 270 Kelvin.

2. The pressure-sensitive adhesive of claim 1 wherein the polyisoprene has a number average molecular weight greater than 200,000.

3. The pressure-sensitive adhesive of claim 1 wherein the polyisoprene comprises 20 to 50 percent of the elastomeric component.

4. The pressure-sensitive adhesive of claim 1 wherein the polyisoprene comprises 30 to 45 percent of the elastomeric component.

5. The pressure-sensitive adhesive of claim 1 wherein the polyisoprene comprises 30 to 50 percent of the elastomeric component, the block copolymer is a linear block copolymer comprised predominantly of diblock and triblock species, the A block has an average molecular weight between 4,000 and 50,000, and the B block has an average molecular weight between about 5,000 and 500,000.

6. The pressure-sensitive adhesive of claim 1 wherein the elastomeric component comprises 35 to 55 weight percent of the functional adhesive mixtures and the tackifying component comprises 45 to 65 weight percent of the functional adhesive mixture.

7. The pressure-sensitive adhesive of claim 6 wherein 25 to 60 weight percent of the functional adhesive mixture is a solid tackifying resin and 0 to 30 weight percent of the functional adhesive mixture is selected from the group consisting of liquid tackifying resin and plasticizing oil.

8. The pressure-sensitive adhesive of claim 7 wherein the tackifying resin is compatible with the polyisoprene components of the adhesive, and the composite midblock glass transition temperature of the adhesive is from 245 to 255 Kelvin.

9. The pressure-sensitive adhesive of claim 8 wherein the tackifying resin is selected from the group consisting of aliphatic hydrocarbon resins, mixed aliphatic/aromatic tackifying resins, polyterprene tackifiers and hydrogenated tackifying resins, and the block copolymer percent diblock is less than 85 percent.

10. The pressure-sensitive adhesive of claim 8 where the plasticizing oil is selected from the group consisting of naphthionic oil and aromatic oils, and the block copolymer percent diblock is less than 75 percent.

11. The pressure-sensitive adhesive of claim 6 wherein 30 to 55 weight percent of the functional adhesive mixture is a solid tackifying resin and 5 to 20 weight percent of the functional adhesive mixture is selected from the group consisting of liquid tackifying resin and plasticizing oil.

12. The pressure-sensitive adhesive of claim 6 wherein 25 to 60 weight percent of the functional adhesive mixture is a solid tackifying resin and 5 to 20 weight percent of the functional adhesive mixture is selected from the group consisting of liquid tackifying resin and plasticizing oil.

13. The pressure-sensitive adhesive of claim 1 wherein 25 to 60 weight percent of the functional adhesive mixture is a solid tackifying resin and 0 to 30 weight percent of the functional adhesive mixture is liquid tackifying resin or plasticizing oil.

14. A pressure-sensitive adhesive tape comprising a backing and coated onto said backing an adhesive layer of a functional adhesive mixture of;
   30 to 60 weight percent of an elastomeric component consisting essentially of 4 to 55 percent polyisoprene having a number average molecular weight of greater than 100,000 and 96 to 45 percent of an AB(A) block copolymer wherein the A block is 10 to 50 percent of the copolymer and comprises a ring alkylated styrene or styrene and the B block is derived primarily from isoprene, said block copolymer comprising less than 95 weight percent diblock copolymer, and
   40 to 70 weight percent of a tackifying component comprising solid tackifying resin, solid tackifying resin with a liquid tackifying resin or plasticizing oil, or solid tackifying resin with liquid tackifying resin and plasticizing oil so as to provide an adhesive mixture having a composite midblock glass transition temperature in the range of 240 to 270 Kelvin.

15. The pressure-sensitive adhesive tape of claim 14 wherein the polyisoprene has a number average molecular weight greater than 200,000.

16. The pressure-sensitive adhesive tape of claim 14 wherein the polyisoprene comprises 20 to 50 percent of the elastomeric component.

17. The pressure-sensitive adhesive tape of claim 14 wherein the polyisoprene comprises 30 to 45 percent of the elastomeric component.

18. The pressure-sensitive adhesive tape of claim 14 wherein the polyisoprene comprises 30 to 50 percent of the elastomeric component, the block copolymer is a linear block copolymer comprised predominantly of diblock and triblock species, the A block has an average molecular weight between 4,000 and 50,000, and the B block has an average molecular weight between about 5,000 and 500,000.

19. The pressure-sensitive adhesive tape of claim 14 wherein the elastomeric component comprises 35 to 55 weight percent of the functional adhesive mixtures and the tackifying component comprises 45 to 65 weight percent of the functional adhesive mixture.

20. The pressure-sensitive adhesive tape of claim 19 wherein 25 to 60 weight percent of the functional adhesive mixture is a solid tackifying resin and 5 to 20 weight percent of the functional adhesive mixture is liquid tackifying resin or plasticizing oil.

21. The pressure-sensitive adhesive tape of claim 19 wherein the adhesive composite midblock glass transition temperature is from 245 to 255 Kelvin.

22. The pressure-sensitive adhesive tape of claim 19 wherein 30 to 55 weight percent of the functional adhesive mixture is a solid tackifying resin and 5 to 20 weight percent of the functional adhesive mixture is selected from the group consisting of liquid tackifying resin and plasticizing oil.

23. The pressure-sensitive adhesive tape of claim 22 wherein the tackifying resin is selected from the group consisting of aliphatic hydrocarbon resins, mixed aliphatic/aromatic tackifying resins, polyterpene tackifiers and hydrogenated tackifying resins, and the block copolymer percent diblock is less than 85 percent.

24. The pressure-sensitive adhesive tape of claim 23 where the plasticizing oil is selected from the group consisting of naphthionic oil and aromatic oils, and the block copolymer percent diblock is less than 75 percent.

25. A diaper consisting of an absorbent pad, a liquid-impermeable outer layer attached to one face of said pad, and a liquid-permeable inner layer attached to an opposite face of said pad, a reinforcing layer attached to said outer layer, and a fastening tab having a free end for attachment to said reinforcing layer, an opposite end of said fastening tab permanently attached to said diaper, said free end comprising a backing and an adhesive layer of a functional adhesive mixture of;

- 30 to 60 weight percent of an elastomeric component consisting essentially of 4 to 55 percent polyisoprene having a number average molecular weight of greater than 100,000 and 96 to 45 percent of an AB(A) block copolymer wherein the A block is 10 to 50 percent of the copolymer and comprises a ring alkylated styrene or styrene and the B block is derived primarily from isoprene, said block copolymer comprising less than 95 weight percent diblock copolymer, and

- 40 to 70 weight percent of a tackifying component comprising solid tackifying resin, solid tackifying resin with a liquid tackifying resin or plasticizing oil, or solid tackifying resin with liquid tackifying resin and plasticizing oil so as to provide an adhesive mixture having a composite midblock glass transition temperature in the range of 240 to 265 Kelvin.

* * * * *